United States Patent [19]
Oono et al.

[11] Patent Number: 4,745,103
[45] Date of Patent: May 17, 1988

[54] HAIR COSMETIC COMPOSITION

[75] Inventors: Tooru Oono; Yuichi Nishida, both of Tokyo, Japan

[73] Assignee: Lion Corporation, Japan

[21] Appl. No.: 740,809

[22] Filed: Jun. 3, 1985

[30] Foreign Application Priority Data

Jun. 29, 1984 [JP] Japan ................. 59-134792

[51] Int. Cl.$^4$ .............................. A61K 7/06
[52] U.S. Cl. .................... 514/23; 514/970; 514/880; 514/971; 514/558; 514/578; 514/724
[58] Field of Search ............... 514/880, 970, 971, 23, 514/558, 578, 724

[56] References Cited

U.S. PATENT DOCUMENTS

| | | | |
|---|---|---|---|
| 3,708,583 | 1/1973 | Winstrom et al. | 514/971 |
| 3,882,243 | 5/1975 | Maeda et al. | 514/970 |
| 4,199,567 | 4/1980 | Rankin | 514/971 |
| 4,405,645 | 9/1983 | Röthlisberger et al. | 514/881 |
| 4,606,913 | 8/1986 | Aronson et al. | 514/880 |

FOREIGN PATENT DOCUMENTS

| | | | |
|---|---|---|---|
| EP102534 | 3/1984 | European Pat. Off. | 514/880 |
| 58-32809 | 2/1983 | Japan | 514/880 |
| 59-190912 | 10/1984 | Japan | 514/971 |

Primary Examiner—Ronald W. Griffin
Attorney, Agent, or Firm—Lorusso & Loud

[57] ABSTRACT

A hair cosmetic composition in the form of a solution, which includes:

(a) a solvent including ethanol;
(b) a hair-growing component which is at least one compound selected from the group consisting of straight chain, higher aliphatic carboxylic acids having an odd number of carbon atoms, derivatives of straight chain, higher aliphatic carboxylic acids having an odd number of carbon atoms, straight chain, higher aliphatic alcohols having an odd number of carbon atoms and derivatives of straight chain, higher aliphatic alcohols having an odd number of carbon atoms; and
(c) a nonionic surfactant having an HLB value of not greater than 10.

22 Claims, No Drawings

HAIR COSMETIC COMPOSITION

This invention relates to a liquid cosmetic composition.

Hair cosmetics such as hair-growing agents contain various ingredients exhibiting hair-growing activity, e.g. a vitamin such as Vitamin E, an amino acid such as serine or methionine, a vasodilator such as an acetylcholine derivative, an anti-inflammatory agent such as lithospermum root extract, a female sex hormone such as estradiol, a skin function stimulant such as cepharanthine, a melanine synthesis catalyst such as copper pantothenate, a keratolytic such as salicylic acid, or the like. These ingredients may serve to assist in the prevention and cure of alopecia.

Hair cosmetics which contain a higher alcohol having an even number of carbon atoms are known. There are, however, no known cases where an aliphatic higher alcohol having an odd number of carbon atoms or a derivative thereof is used in a hair cosmetic such as hair-growing agent. There are also known cases where an aliphatic carboxylic acid or a derivative thereof such as natural vegetable oil, e.g. olive oil and castor oil, or stearic acid is contained in a hair cosmetic such as a hair-growing agent or the like to improve the performance of the product. Such aliphatic carboxylic acids are, in almost all cases, ones that have an even number of carbon atoms. Japanese Published Unexamined Patent Application No. 59-27809 suggests the use of a fatty acid with an odd number of carbon atoms or a derivative thereof as an effective ingredient of a hair-growing agent. While the hair-growing agent of the above Japanese publication exhibits a potent hair-growing effect, the preservability thereof, especially under cold conditions, has been found not to be entirely satisfactory in practice. More particularly, it has been found that when the hair-growing agent is stored at a low temperature of, for example, 0° to −5° C., for a long period of time, the agent becomes cloudy due to the formation of crystals of the hair-growing ingredient, causing the lowering of the absorbability of the ingredient through the skin and, therefore, the reduction of the hair-growing effect.

The present invention has been made from a consideration of the above-described problem. In accordance with the present invention, there is provided a composition in the form of a solution useful as a hair cosmetic, which includes:

(a) a solvent including ethanol;

(b) a hair-growing component which is at least one compound selected from the group consisting of straight chain, higher aliphatic carboxylic acids having an odd number of carbon atoms, derivatives of the higher aliphatic carboxylic acids, straight chain, higher aliphatic alcohls having an odd number of carbon atoms, and derivatives of the higher aliphatic alcohols; and (c) a nonionic surfactant having an HLB value of not greater than 10.

The potent hair-growing effect of the carboxylic acids, alcohols and their derivatives are considered to be attributed to their following properties: firstly, these compounds are soluble in lipids of the hair follicles so that they can easily penetrate through the skin and reach to the root of hair; secondly, these compounds are not susceptible to the metabolic decomposition by phospholactokinase; and thirdly, these compounds serve to activate metabolism and efficiently produce energy.

The straight chains of the higher aliphatic carboxylic acids and higher aliphatic alcohols used in the present invention may be saturated or unsaturated, provided that they have an odd number of carbon atoms. The unsaturated aliphatic chains may contain two or more double bonds. Preferably, the higher aliphatic carboxylic acids and alcohols have at least 9 carbon atoms, more preferably from 11 to 17 carbon atoms. The amount of the hair-growing component in the composition is generally in the range of 0.1–10 wt %, preferably 1–5 wt %.

Preferably, the hair-growing component is at least one compound selected from those represented by the following general formulae (I) through (III):

(I)

wherein $R_1$ stands for a straight chain aliphatic group having 8 or more, even numbered carbon atoms, most preferably 10, 12, 14 or 16 carbon atoms, $X_1$ stands for —O— or

where $R_4$ represents hydrogen or an organic group, and $Y_1$ stands for hydrogen, an organic group or an inorganic group;

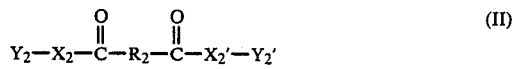
(II)

wherein $R_2$ stands for a straight chain aliphatic group having 7 or more, odd numbered carbon atoms, most preferably 9, 11, 13 or 15 carbon atoms, $X_2$ and $X_2'$ stand independently for —O— or

where $R_5$ represents hydrogen or an organic group, and $Y_2$ and $Y_2'$ stand independently for hydrogen, an organic group or an inorganic group, and

(III)

wherein $R_3$ stands for a straight chain aliphatic group having 9 or more, odd numbered carbon atoms, most preferably 11, 13, 15 or 17 carbon atoms, and $Y_3$ stands for hydrogen, an organic group or an inorganic group.

Suitable examples of the compounds of the general formula (I) include:

(1) Fatty acid such as undecanoic acid, tridecanoic acid, pentadecanoic acid and heptadecanoic acid;

(2) Metal salts such as alkali metal salts of the fatty acids shown in (1) above;

(3) Mono-, di and triglycerides of the following formula (IV) or (V)

$$\begin{array}{ll} CH_2-O-CO-R_1 & CH_2-O-Y_6 \\ CHO-Y_4 & CH-O-CO-R_1 \\ CH_2-O-Y_5 & CH_2-O-Y_7 \\ \quad (IV) & \quad (V) \end{array}$$

where $Y_3$, $Y_5$, $Y_6$ and $Y_7$ represent independently hydrogen, an organic group or an inorganic group. Illustrative of the glycerides are as follows:

$$\begin{array}{lll} CH_2OCOR_1 & CH_2OCOR_1' & CH_2OCOR_1 \\ CHOCOR_1' & CHOCOR_1 & CHOH \\ CH_2OH & , CH_2OH & , CH_2OH \end{array},$$

$$\begin{array}{lll} CH_2OH & CH_2OCOR_1 & CH_2OCOR_1 \\ CHOCOR_1 & CHOH & CHOCOR_1' \\ CH_2OH & , CH_2OCOR_1' & , CH_2OCOR_1'' \end{array},$$

$$\begin{array}{lll} CH_2OCOR_1' & CH_2OCOR_1 & CH_2OCOR_1' \\ CHOCOR_1 & CHOCOR_1' & CHOCOR_1 \\ CH_2OCOR_1'', & H_2C-O\!\!\diagdown\!\!P(=O)(O^-)\!\!-\!O^-, & H_2C-O\!\!\diagdown\!\!P(=O)(O^-)\!\!-\!O^-, \end{array}$$

$$\begin{array}{ll} CH_2OCOR_1 & CH_2OCOR_1' \\ CHOCOR_1' & CHCOR_1 \\ H_2C-O\!\!\diagdown\!\!P(=O)(L)\!\!-\!O^- \text{ and } & H_2C-O\!\!\diagdown\!\!P(=O)(L)\!\!-\!O^- \end{array}$$

where $R_1'$ and $R_1''$ each represent an aliphatic group, preferably a straight chain aliphatic group having an even number of carbon atoms and L represents choline residue, an ethanolamine residue, a serine residue or an inositol residue;

(4) Esters of the formula $$R_1CO-O-Y_1$$

wherein $Y_1$ stands for a residue of a primary or secondary alcohol, an ethanolamine residue, a polyoxyethylene residue, a sorbitan residue, a sucrose residue or a sterol residue. An example of the sterol ester is as shown below:

[sterol structure with $R_1COO-$ substituent]

(5) Primary amides of the formula $$R_1CO-N(R_4)-R_4'$$

wherein $R_4$ and $R_4'$ represent independently hydrogen or an organic group;

(6) Secondary amides of the formula $$R_1CO-N(R_4)-CO-R_5$$

wherein $R_4$ represents hydrogen or an organic group and (7) Tertiary amides of the formula $$R_1-CO-N(CO-R_6)-CO-R_5$$

wherein $R_5$ and $R_6$ each represent an organic group, preferably an aliphatic group having even number of carbon atoms.

A suitable example of the compound of the general formula (II) is an aliphatic dicarboxylic acid of the formula $$HOOC-R_2-COOH$$

Suitable examples of the compounds of the general formula (III) include:

(1) Carboxylic acid esters represented by the formula $$R_3O-\underset{\underset{O}{\|}}{C}-Y_8$$

wherein $Y_8$ represents a carboxylic acid residue;

(2) Inorganic acid esters of the formula $$R_3O-Y_3$$

wherein $Y_3$ represents an inorganic acid residue. Illustrative of the carboxylic acid residues are residues of fatty acids with 2-24 carbon atoms, succinic acid, fumaric acid, lactic acid, pyruvic acid, malic acid and oxaloacetic acid. Illustrative of the inorganic acid residue is a phosphoric acid residue; and (3) Ethers of an aliphatic alcohol $R_3$—OH and a primary or secondary alcohol or a sugar, such as primary alcohols with 2-24 carbon atoms, glycerin, polygrycerin, ethylene glycol, propylene glycol, butane diol, glucose, ribose, galactose, arabinose, mannose, xylose, sorbitol and mannitol.

The term "residue" such as "alcohol residue" or "carboxylic acid residue" used in the present specification is intended to mean a compound such as an alcohol or a carboxylic acid from which the functional group such as —OH or —COOH has been removed. For example, an ethylene glycol residue, a triethanolamine residue, a choline residue, a serine residue and a succinic acid residue mean —CH$_2$CHOH, —CH$_2$CH$_2$N(CH$_2$C-H$_2$OH)$_2$,

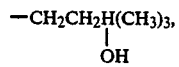

—CH$_2$CH(NH$_2$)COOH and —CH$_2$CH$_2$COOH, respectively.

In the hair cosmetic composition according to the present invention, the hair-growing component described above is used together with a nonionic surfactant having an HLB value of 10 or less.

The term "HLB value" is used in the present specification is described in detail in J. Soc. Cosmetic Chemist's, vol 5, 249 (1954). Illustrative of suitable nonionic surfactants are fatty acid esters of sorbitan, fatty acid esters of polyoxyethylene sorbitan ethers, fatty acid esters of polyoxyethylene sorbit ethers, polyoxyethylene-hardened castor oil, fatty acid esters of polyoxyethylene-hardened castor oil, fatty acid esters of polyglycerin ethers, N-(long chain acyl)-L-glutamic acid diesters of higher alcohols, N-(long chain acyl)-L-glutamic acid diesters of polyoxyethylene higher alcohol ethers. The HLB values of these nonionic surfactants are variable by changing their contents of ethylene oxide or propylene oxide units or the length of their lipophile groups. In order to impart excellent reservability of the hair cosmetic composition, the HLB value of the nonionic surfactant must be 10 or less. The content of the nonionic surfactant in the composition is generally in the range of 0.1–10 wt %, preferably 0.5–5 wt %.

The hair-growing component and the nonionic surfactant are dissolved in an ethanol-containing solvent to provide the composition of the present invention. The solvent is preferably an aqueous ethanol containing 50–95, preferably 70–90 wt % of ethanol.

The hair cosmetic composition may contain various other auxiliary ingredients such as polyol, fatty oils, fats and surfactants and various conventional hair-growing ingredients such as vitamins, hormones, vasodilators, amino acids, antiinflammatory agents, skin function stimulants and keratolytics. The hair cosmetic composition according to the present invention may be used in a variety of forms such as a hair-growing agent, a hair tonic, a shampoo, a hair lotion and a hair liquid.

The following examples will further illustrate the present invention.

EXAMPLE 1

Nineteen kinds of hair-growing agents having compositions shown in Table 1 or 2 were prepared and tested for the evaluation of their hair-growing activity and stability against low temperature conditions. The results are summarized in Tables 1 and 2. In Tables 1 and 2, the abbreviation "POE" means polyoxyethylene and the numerals in the parentheses immediately after the letters POE mean the number (mole number) of the ethylene oxide unit of the polyoxyethylene. The hair-growing activity and stability were tested as follows:

Evaluation of Hair-Growing Activity

The test animals were groups of 6 to 8 male rabbits of New Zealand White species each weighing about 2.5 Kg and each having its back hair removed. Rabbits in the telogen state alone were used. The test specimen was applied in the amount of 0.2 ml twice per week for 30 to 60 days to the area of the rabbits' backs from which the hair had been removed. The number of days required for the conversion of hair from the telogen state into the anagen state was measured to calculate shortened days which means the number of days by which the conversion of the telogen state into anagen state is shortened, as compared with the control in which ethanol containing no test substance was applied. For example, shortened days of 10 means that the conversion of telogen state into anagen state occurred 10 days earlier than the control.

Evaluation of Stability Against Low Temperature Condition

The test sample (about 50 g) in a colorless, transparent glass tube was allowed to stand at −5° C. for 30 days. Then, the resultant sample was observed to determine whether or not the crystallization or cloudiness took place. The stability was rated as follows:

A: Stable: No crystals were formed and the sample did not become cloudy.
B: Unstable: Crystals were formed in trace amount.
C: Considerably Unstable: The sample became cloudy or crystals were formed in a significant amount.

TABLE 1

| | No 1* | No 2* | No 3* | No 4 | No 5 | No 6 | No 7 | No 8 | No 9 | No 10 |
|---|---|---|---|---|---|---|---|---|---|---|
| Hair-growing component | 3 | 3 | 3 | 3 | 3 | 3 | 3 | 3 | 3 | 3 |
| Glyceryl monopentadecanoate | | | | | | | | | | |
| Nonionic surfactant | | | | | | | | | | |
| (1) POE(60) sorbit tetraoleate | 3 | | | | | | | | | |
| (2) POE(40) sorbit tetraoleate | | 3 | | | | | | | | |
| (3) POE(30) sorbit tetraoleate | | | 3 | | | | | | | |
| (4) POE(6) sorbit tetraoleate | | | | 0.1 | 3 | 10.0 | | | | |
| (5) Sorbitan monolaurate | | | | | | | 3 | | | |
| (6) Sorbitan monooleate | | | | | | | | 3 | | |
| (7) POE(10) hardened castor oil monoisostearate | | | | | | | | | 3 | |
| (8) N—lauroylglutamic acid POE(2) octyl dodecyl ether | | | | | | | | | | 3 |
| Solvent | balance | balance | balance | balance | balance | balance | balance | balance | balance | balance |
| 99.5% Ethanol | | | | | | | | | | |
| HLB value of the surfactant | 14.0 | 12.5 | 11.5 | 8.5 | 8.5 | 8.5 | 8.6 | 4.3 | 3.8 | 1.8 |
| Hair-growing activity Shortened days | 30 | 30 | 30 | 30 | 30 | 30 | 30 | 30 | 30 | 30 |
| Stability | C | C | B | A | A | A | A | A | A | A |

| | Contents (wt %) | | | | | | | | |
|---|---|---|---|---|---|---|---|---|---|
| | No 11 | No 12 | No 13 | No 14 | No 15 | No 16 | No 17* | No 18* | No 19* |
| Hair-growing component | | | | | | | | | |

TABLE 1-continued

| | | | | | | | | | |
|---|---|---|---|---|---|---|---|---|---|
| (1) Tridecanoic acid | 0.3 | | | | | | | | |
| (2) Pentadecanoic acid | | 0.3 | | | | | | | |
| (3) Heptadecanoic acid | | | 0.3 | | | | | | |
| (4) Tridecyl alcohol | | | | 1.0 | | | 1.0 | | |
| (5) Pentadecyl alcohol | | | | | 1.0 | | | 1.0 | |
| (6) Heptadecyl alcohol | | | | | | 1.0 | | | 1.0 |
| Nonionic surfactant | | | | | | | | | |
| (1) POE(20) hardened castor oil monoisostearate | 1.0 | 1.0 | 1.0 | 1.0 | 1.0 | 1.0 | | | |
| (2) POE(50) hardened castor oil monoisostearate | | | | | | | 1.0 | 1.0 | 1.0 |
| Solvent | | | | | | | | | |
| (1) 99.5% Ethanol | 70 | 70 | 70 | 70 | 70 | 70 | 70 | 70 | 70 |
| (2) Pure water | balance | balance | balance | balance | balance | balance | balance | balance | balance |
| HLB value of the surfactant | 7.0 | 7.0 | 7.0 | 7.0 | 7.0 | 7.0 | 12.0 | 12.0 | 12.0 |
| Shortened days | 20 | 20 | 20 | 20 | 20 | 20 | 20 | 20 | 20 |
| Stability | A | A | A | A | A | A | B | B | B |

EXAMPLE 2

A hair-growing agent, a hair tonic and a hair liquid having the formulations shown below were prepared. These cosmetics were found to have an excellent stability against low temperature conditions.

| Hair-growing agent: | |
|---|---|
| Gryceryl monopentadecanoate | 3 wt % |
| di-α-Tocopherol acetate | 0.2 |
| Pyridoxine dicaprylate | 0.1 |
| Patentothenyl alcohol | 0.5 |
| Ethynylestradiol | 0.0004 |
| Safflower oil | 0.5 |
| 6-[2-[(5-Bromo-2-pyridyl)amino]vinyl]-1-ethyl-2-picolinium iodide | 0.005 |
| Biotin | 0.05 |
| Swertia japonica extract | 0.01 |
| Swertinogen | 0.01 |
| Hinokitiol | 0.1 |
| Diglyceryl diisostearate | 2 |
| Sorbitan monolaurate | 2 |
| Succinic acid | 0.3 |
| Perfume | 0.5 |
| 99.5% Ethanol | Balance |
| Hair liquid: | |
| Ethyl n-tridecanoate | 1 wt % |
| Polyoxypropylene butyl ether (oxypropylene: 40 moles) | 15 |
| Sodium salicylate | 0.1 |
| Isopropylmethylphenol | 0.1 |
| Aloe extract | 0.1 |
| Nard oil | 0.05 |
| POE(20) hardened castor oil monoisostearate | 1 |
| Perfume | 0.5 |
| 95% Ethanol | 55 |
| Pure water | Balance |
| Hair tonic: | |
| N—(hydroxyethyl)pentadecanamide | 0.1 wt % |
| n-Nonanoic acid | 0.1 |
| Tridecyl alcohol | 1 |
| Chloroxylenol | 0.1 |
| Benzyl nicotinate | 0.001 |
| l-Menthol | 0.1 |
| Sorbitan monooleate | 0.1 |
| Glycyrrhizinic acid monoammonium | 0.1 |
| Perfume | 0.5 |
| 95% Ethanol | 75 |
| Pure water | Balance |

We claim:

1. A composition of matter in the form of a solution, comprising:
(a) a solvent including ethanol;
(b) a hair-growing component which is at least one compound selected from the group consisting of:

$$R_1-\overset{O}{\underset{\|}{C}}-X_1-Y_1 \qquad (1)$$

wherein
$R_1$ is a straight chain aliphatic group having 8 or more even numbered carbon atoms,
$X_1$ is —O— or $$-\underset{R_4}{\overset{|}{N}}-$$

where $R_4$ represents hydrogen or an organic group, and
$Y_1$ is hydrogen, an organic group or an inorganic group;

$$Y_2-X_2-\overset{O}{\underset{\|}{C}}-R_2-\overset{O}{\underset{\|}{C}}-X_2'-Y_2' \qquad (2)$$

wherein
$R_2$ is a straight chain aliphatic group having 7 or more, odd numbered carbon atoms,
$X_2$ and $X_2'$ are independently —O— or $$-\underset{R_5}{\overset{|}{N}}-$$

where $R_5$ represents hydrogen or an organic group and
$Y_2$ and $Y_2'$ are independently hydrogen, an organic group or an inorganic group; and $$R_3-O-Y_3 \qquad (3)$$

wherein
$R_3-O-Y_3$ is a straight chain aliphatic group having 9 or more odd numbered carbon atoms,
$Y_3$ is hydrogen, an organic group or an inorganic group; and
(c) a nonionic surfactant having an HLB value of not greater than 10.

2. A composition as claimed in claim 1, wherein $X_1$ stands for —O—, $Y_1$ stands for hydrogen and $R_1$ stands for decyl, dodecyl, tetradecyl or hexadecyl.

3. A composition as claimed in claim 1, wherein $X_1$ stands for —O— and $Y_1$ stands for

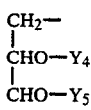

where $Y_4$ and $Y_5$ represent independently hydrogen, an organic group or an inorganic group.

4. A composition as claimed in claim 3, wherein at least one of the groups $Y_4$ and $Y_5$ represents

where $R_1$ has the same meaning as above.

5. A composition as claimed in claim 3, wherein $Y_4$ represents a straight chain aliphatic group and $Y_5$ represents

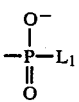

where $L_1$ represents $O^-$ or $O—L_2$ where $L_2$ represents a choline residue, an ethanolamine residue, a serine residue or an inositol residue.

6. A composition as claimed in claim 1, wherein $X_1$ stands for —O— and $Y_1$ stands for

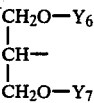

where $Y_6$ and $Y_7$ represent independently hydrogen, an organic group or an inorganic group.

7. A composition as claimed in claim 6, wherein $Y_6$ represents a straight chain aliphatic group and $Y_7$ represents

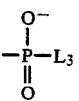

where $L_3$ represents $O^-$ or $O—L_4$ where $L_4$ represents a choline residue, an ethanolamine residue, a serine residue or an inositol residue.

8. A composition as claimed in claim 1, wherein $X_1$ stands for —O— and $Y_1$ stands for an alkali metal or

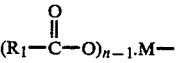

where $R_1$ has the same meaning as above, M is a metal and n is the valance of the metal M.

9. A composition as claimed in claim 1, wherein $X_1$ stands for —O— and $Y_1$ stands for a residue of a primary or secondary alcohol, an ethanolamine residue, a polyoxyethylene residue, a sorbitan residue or a sucrose residue.

10. A composition as claimed in claim 1, wherein $X_1$ is —O— and $Y_1$ is an organic group having a steroid skelton.

11. A composition as claimed in claim 1, wherein $X_1$ is

and $Y_1$ stands for

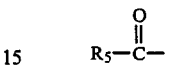

where $R_5$ represents an organic group.

12. A composition as claimed in claim 11, wherein $R_4$ represents

where $R_6$ represents an organic group.

13. A composition as claimed in claim 1, wherein $X_1$ stands for —NH— and $Y_1$ stands for

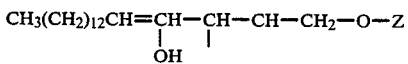

where Z represents a sugar residue, a phosphate residue, a choline residue or an ethanolamine residue.

14. A composition as claimed in claim 1, wherein $X_2$ and $X_2'$ each stands for —O— and $Y_2$ and $Y_2'$ each stand for hydrogen.

15. A composition as claimed in claim 1, wherein $Y_3$ stands for

where $Y_8$ represents a carboxylic acid residue or for an inorganic acid residue.

16. A composition as claimed in claim 15, wherein $Y_8$ represents a residue of a fatty acid having 2–24 carbon atoms, succinic acid, fumaric acid, lactic acid, pyruvic acid, malic acid or oxaloacetic acid and said inorganic acid residue is a phosphoric acid residue.

17. A composition as claimed in claim 1, wherein $Y_3$ stands for a residue of primary or secondary alcohol or a sugar residue.

18. A composition as claimed in claim 17, wherein $Y_3$ stands for a residue of a primary alcohol having 2–24 carbon atoms, glycerin, polyglycerin, ethylene glycol, propylene glycol, butane diol, glucose, ribose, galactose, arabinose, mannose, xylose, sorbitol or mannitol.

19. A composition as claimed in claim 1, wherein the amount of said hair-growing component is in the range of 0.1–10 weight %.

20. A composition as claimed in claim 1, wherein said surfactant is selected from the group consisting of fatty acid esters of sorbitan, fatty acid esters of polyoxyethylene sorbitan ethers, fatty acid esters of polyoxyethylene sorbit ethers, polyoxyethylene-hardened castor oil, fatty acid esters of polyoxyethylene-hardened castor oil, fatty acid esters of polyglycerin ethers, N-(long chain acryl)-L-glutamic acid diesters of higher alcohols, N-(long chain acryl)-L-glutamic acid diesters of polyoxyethylene higher alcohol ethers.

21. A composition as claimed in claim 1, wherein the amount of said surfactant is in the range of 0.1–10 weight %.

22. A composition as claimed in claim 1, wherein said solvent is an aqueous ethanol solution containing 50–95% by weight of ethanol.

* * * * *

UNITED STATES PATENT AND TRADEMARK OFFICE
CERTIFICATE OF CORRECTION

PATENT NO. : 4,745,103

DATED : May 17, 1988

INVENTOR(S) : OONO et al

It is certified that error appears in the above-identified patent and that said Letters Patent is hereby corrected as shown below:

Column 1, line 57, "alcohls" should read --alcohols--.

Column 3, lines 32-40 the formula reading:

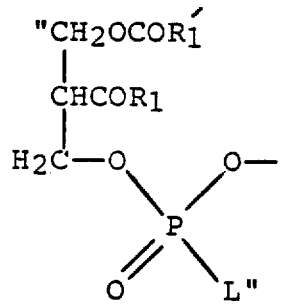

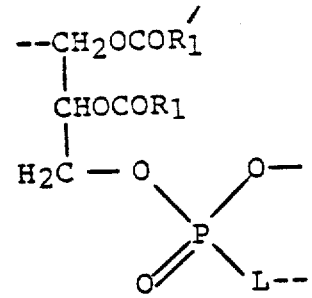

Should read:

Signed and Sealed this

Fourth Day of October, 1988

Attest:

DONALD J. QUIGG

Attesting Officer

Commissioner of Patents and Trademarks